United States Patent [19]
Paul

[11] Patent Number: 5,264,026
[45] Date of Patent: Nov. 23, 1993

[54] CENTRALIZED LASER PLUME EVACUATION SYSTEM THROUGH ARTICULATING ARMS

[75] Inventor: Gwen A. Paul, Minneapolis, Minn.

[73] Assignee: Michaud, Cooley, Erickson & Associates, Minn.

[21] Appl. No.: 985,823

[22] Filed: Dec. 3, 1992

[51] Int. Cl.⁵ .................. B01D 45/12; B01D 46/10
[52] U.S. Cl. .................................... 95/268; 95/271; 95/273; 55/385.1; 55/418; 55/459.1; 55/467; 604/21; 604/322
[58] Field of Search ............... 55/97, 315, 357, 385.1, 55/418, 459.1, 467; 604/21, 313, 319, 322

[56] References Cited

U.S. PATENT DOCUMENTS

| | | | |
|---|---|---|---|
| 1,936,129 | 11/1933 | Fisk | 604/313 |
| 2,074,481 | 3/1937 | Macmullen et al. | 55/503 X |
| 2,162,019 | 6/1939 | Johnson | 98/115 |
| 3,841,145 | 10/1974 | Boubel | 55/503 X |
| 3,955,236 | 5/1976 | Mekelburg | 55/337 X |
| 4,082,092 | 4/1978 | Foster | 604/313 X |
| 4,133,658 | 1/1979 | Callewyn | 55/337 X |
| 4,158,462 | 6/1979 | Coral | 285/168 |
| 4,163,650 | 8/1979 | Watson et al. | 55/126 |
| 4,345,342 | 8/1982 | Saito | 604/319 X |
| 4,446,861 | 5/1984 | Tada | 128/139 |
| 4,503,854 | 3/1985 | Jako | 128/303.1 |
| 4,512,245 | 4/1985 | Goldman | 98/115.4 |
| 4,540,202 | 9/1985 | Amphoux et al. | 285/184 |
| 4,541,327 | 9/1985 | Lundström | 98/115.4 |
| 4,581,050 | 4/1986 | Krantz | 55/337 X |
| 4,619,672 | 10/1986 | Robertson | 55/316 |
| 4,642,128 | 2/1987 | Solorzano | 55/467 X |
| 4,685,944 | 8/1987 | Allan et al. | 55/503 X |
| 4,701,193 | 10/1987 | Robertson et al. | 55/217 |
| 4,737,173 | 4/1988 | Kudirka et al. | 55/276 |
| 4,810,269 | 3/1989 | Stackhouse et al. | 55/267 |
| 4,865,629 | 9/1989 | Zievers et al. | 55/337 X |
| 4,905,578 | 3/1990 | Curtis et al. | 98/1.5 |
| 4,906,261 | 3/1990 | Mohajer | 55/467 X |
| 4,963,134 | 10/1990 | Backscheider et al. | 604/319 |
| 4,976,694 | 12/1990 | Schreibman | 604/319 X |
| 4,986,839 | 1/1991 | Wertz et al. | 55/274 |
| 5,015,243 | 5/1991 | Schifano | 604/315 |
| 5,047,072 | 9/1991 | Wertz et al. | 55/1 |
| 5,145,496 | 9/1992 | Mellen | 55/337 X |

FOREIGN PATENT DOCUMENTS

WO89/11885  12/1989  PCT Int'l Appl. .................. 604/313

Primary Examiner—Robert Spitzer
Attorney, Agent, or Firm—Moore & Hansen

[57] ABSTRACT

A centralized system for removing the plume resulting from laser surgery, electrocauterization or orthopaedic surgery that takes advantage of the articulating arms frequently found in medical procedure rooms. The plume is drawn away from the surgery location by a vacuum. The tubing that carries the plume is held near the location of the medical procedure, and the plume is then drawn into the tubing. The tubing leads through the articulating arm to a main located above the ceiling. The main leads to a central room that includes, in series, a centrifugal separator, a vacuum producer and a high efficiency air filter.

36 Claims, 7 Drawing Sheets

CENTRALIZED LASER PLUME EVACUATION SYSTEM THROUGH ARTICULATING ARMS

BACKGROUND OF THE INVENTION

1. Technical Field

The present invention relates generally to systems for the removal of airborne contaminants, such as vaporized tissue and other debris, that result from laser surgery and other surgeries that generate fumes or airborne debris.

2. Background Information

In the process of performing various forms of laser surgery, orthopaedic surgery or electrocauterization, common by-products are airborne fumes and particles, either wet or dry. For example, in the case of orthopaedic surgery, blood and debris rises from the cutting area, while in the case of laser surgery, the matter rising from the area of the operation is vaporized tissue. These by-products rise from the site of the surgery in the form of a plume, the by-products sometimes also being referred to as smoke, although they are not the result of combustion in the ordinary sense of the word. In the case of odors resulting from the lasing of organic tissue, for example, those odors are capable of lingering in the operating room for an extended time following the completion of the surgery.

Of greater concern than lingering odors, however, are the germs and viruses that may also linger in the air following the operation. These disease-carrying particles, if allowed to remain airborne in the operating room, may settle into the open wounds of the next patient being operated on, potentially resulting in the transmission of that disease to the next patient. As of the present time, it remains unclear to what extent these airborne viruses pose a threat to later patients of the operating room, although it is known that at least one virus, Human Papillomavirus DNA (HPV DNA), a wart virus, does survive the laser surgery procedure and may pose a health risk if allowed to linger in the operating room. Of potentially greater concern is the HIV virus that causes AIDS. While no conclusive evidence has yet been found that the HIV virus survives the laser surgery procedure, there is also no such evidence that it does not. Additionally, there is a risk of HIV contamination due to aerosolized blood and tissue debris, resulting from laser or orthopaedic procedures, which may remain in the air of the room where the medical procedure has been performed.

More existing laser plume filtration systems are portable units that may be moved from operating room to operating room, as needed. They provide useful filtration features, but the treated air is recirculated back into the operating room, where microscopic particulate matter that escaped the filtration process remains for the next operating procedure. It is known to use portable units for filtration, and then exhaust the treated air outside of the operating room, but this is not commonly done because of the added inconvenience of properly configuring such a system. Further, the portable units frequently lack the system power to draw all of the airborne debris into the filtration unit in the first place.

One of the other problems with portable laser plume filtration systems of the prior art is that they frequently take up precious floor space in a busy operating room, requiring doctors and nurses to walk around them. In addition, if such a unit is placed off to the side of the room to keep it out of the way, then hoses must be connected to it leading to the patient, and the hoses then become an obstacle to contend with in the operating room. In addition, since these units are self contained, including motorized vacuum pumps, they tend to be quite noisy, detracting from the feeling of order that is desirable in an operating room during surgery.

Manufacturers of portable units, in an effort to enhance portability and minimize size requirement, are often forced to minimize the vacuum power of the units. The effect, however, is to tend to reduce the portable unit's ability to draw all airborne particles into the filtration system, resulting in reduced effectiveness of the system.

The centralized laser plume evacuation system of the present invention overcomes difficulties described above and affords other features and advantages heretofore not available.

SUMMARY OF THE INVENTION

The centralized laser plume evacuation system of the present invention operates preferably through articulating arms in a medical procedure room, although it may also be accessed through wall or ceiling outlets or through a medical gas column. Some hospitals, for example, have three articulating arms in each operating room. These articulating arms are fastened to and suspended from the ceiling of the operating room, and provide all medical gas services, as well as high pressure air for tool use. Electrical services within these arms include outlets and video jacks. The articulating arms are motorized and provide a range of motion, both vertically and horizontally.

The centralized laser plume evacuation system is preferably installed in an articulating arm in each procedure room. On the face of each articulating arm, there is a panel for medical gas outlets. The lower area of one panel is dedicated to providing access to the centralized laser plume evacuation system. On this panel, there is a hinged outlet to the vacuum system, as well as a user adjustable capacity control.

Evacuation takes place through flexible plastic tubing, similar to and interchangeable with the tubing used for portable systems. This tubing is available with inside diameters ranging from ⅛ inch (3.125 mm) to 1¼ inch (31.25 mm). A range of tubes should be stocked to allow for use for different procedures. The largest tubing will allow for the best evacuation from surface procedures. The smallest tubing is used for connection to the laparoscope. This flexible tubing is sterile and packaged for use. This tubing is then disposed of following a procedure.

The connector between the tubing and the outlet is a gasketed rigid fitting. This fitting is held into the outlet by a tooth on the hinged outlet. The intake size of this fitting varies depending on tubing size. Within this connector, there is an integral screen designed to capture any needles or sponges that may be picked up by the system.

The central components of the system include a centrifugal separator tank, garbage pump, optional disinfectant tank, vacuum producer (fan) and HEPA filter. The operating rooms are connected to the central components by a piping system that has branch takeoffs that serve all of the outlets. The piping system includes the flexible plastic tubing discussed above, as well as permanent piping. The initial part of the permanent piping system is additional flexible tubing located within the articulating arm. This tubing must be flexible to allow for movement and rotation of the arm. The inner walls of the tubing must be smooth so debris cannot build up. The flexible tubing connects into copper piping, which feeds into the main piping, all of which is located in the ceiling. All branch piping is designed with 45 degree long sweep connections into the main piping. The main piping should have long radius elbows at every 90 degree turn. Piping cleanouts should be provided at every elbow to provide access to the piping system in case of blockage. Finally, the piping system also accommodates future expansion of and connectivity to the system.

The central system components are located in a mechanical room, central to the operating rooms served by the laser plume evacuation system. The piping mains join together and are connected to the centrifugal separator tank. The tank separates debris picked up by the system from the air passing through the system. The debris, which includes vaporized tissue particles, bone dust, etc. is flushed out of the tank, through a small garbage pump, and into the sanitary sewer system. Air leaves the top of the separator tank and is drawn through the vacuum producers before entering the HEPA filter. The purpose of the filter is to capture particles before air is discharged to the outside air. The HEPA filter captures particles 0.10 microns and greater. This filter is easily removable and should be changed periodically by maintenance personnel.

It is an object of this invention to provide an efficient, convenient, easily accessible system for evacuating airborne contaminants from a hospital operating room. It is a further object of this invention to provide such a system that also exhausts the air out of the hospital operating room rather than recirculating it back into the room. It is also an object of this invention to provide such a system that is quiet, reducing any disruption that might be added to the hospital operating room brought on by loud machinery. Perhaps the most important object of this invention is to provide a laser plume evacuation system that ensures the removal of airborne germs and viruses, greatly reducing the likelihood of transmission of contagious diseases from one patient to the next.

Other objects and advantages of the invention will become apparent from the following detailed description and from the appended drawings in which like numbers have been used to describe like parts throughout the several views.

DESCRIPTION OF THE PREFERRED EMBODIMENT

Figure 1:
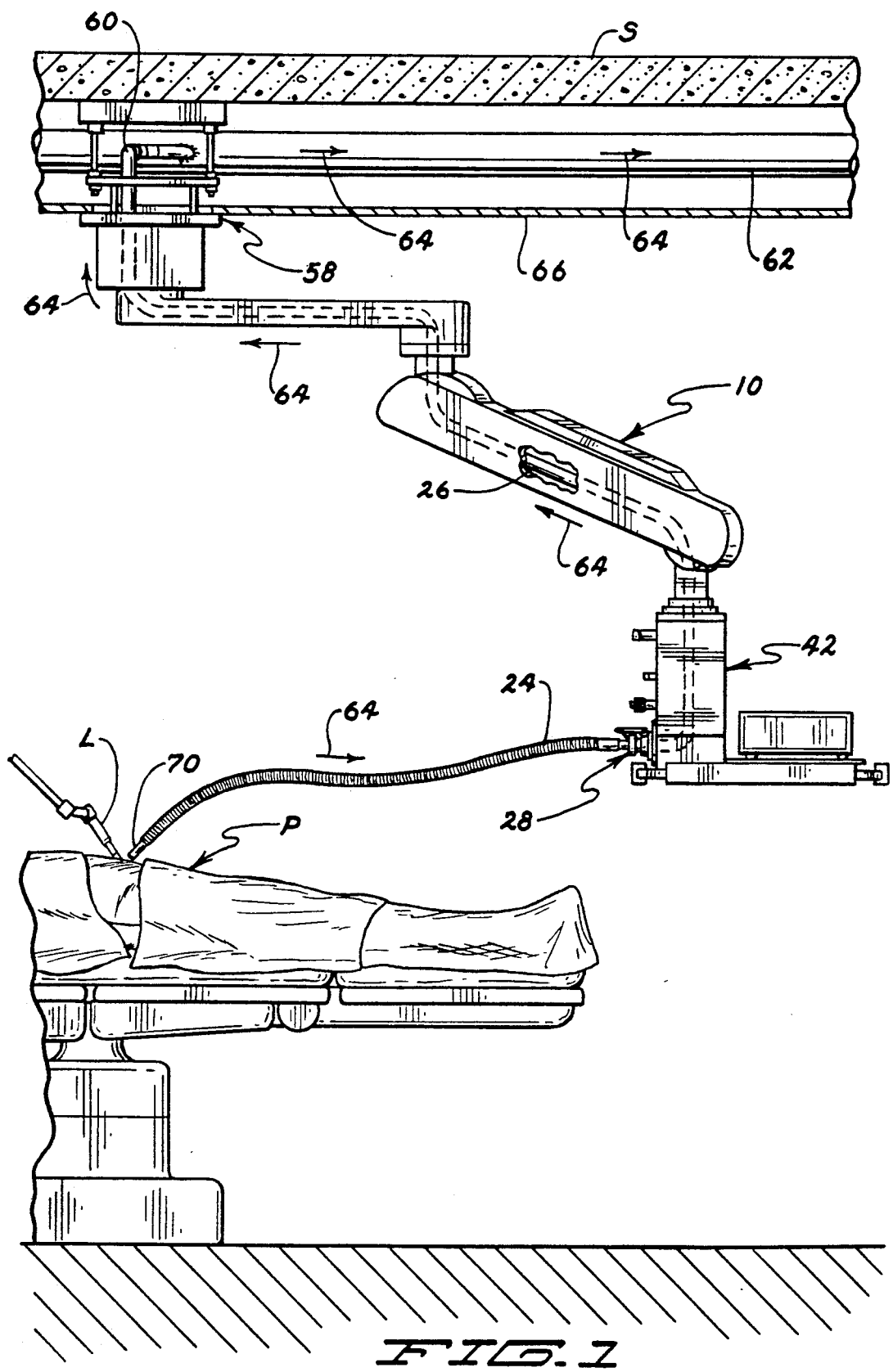
FIG. 1 shows a partially broken away view of an articulating arm in a hospital operating room, the articulating arm being equipped with and connected to flexible hose and piping of the centralized laser plume evacuation system.
Figure 2:
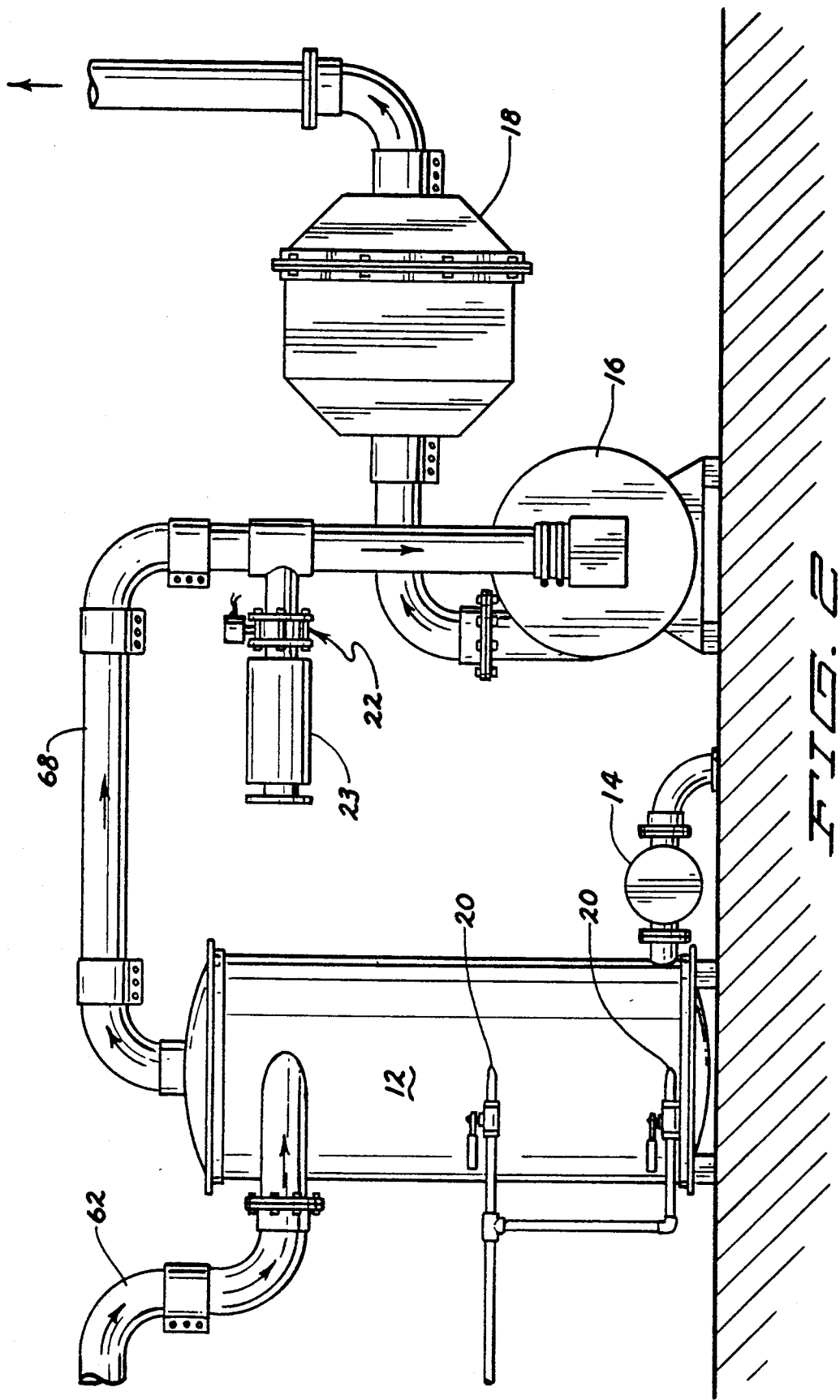
FIG. 2 shows a side view of a typical layout of a hospital mechanical room equipped with the central components of the present invention.

With reference to the drawings, and in particular to FIG. 1, the articulating arm through which the centralized laser plume evacuation system is accessed in the preferred embodiment is generally indicated by reference numeral 10. Referring to FIG. 2, the other main components of the system include a centrifugal separator tank 12, a garbage pump 14, a vacuum producer or fan 16, and a HEPA filter 18. The system may optionally include a disinfectant tank, not shown. Finally, to accommodate use of the system by varying numbers of operating rooms, bleed valve 22 is provided to permit adequate volumes of air to be drawn into the system to satisfy vacuum producer 16. A silencer 23 may also be provided to reduce the noise resulting from operation of the bleed valve.

Figure 3:
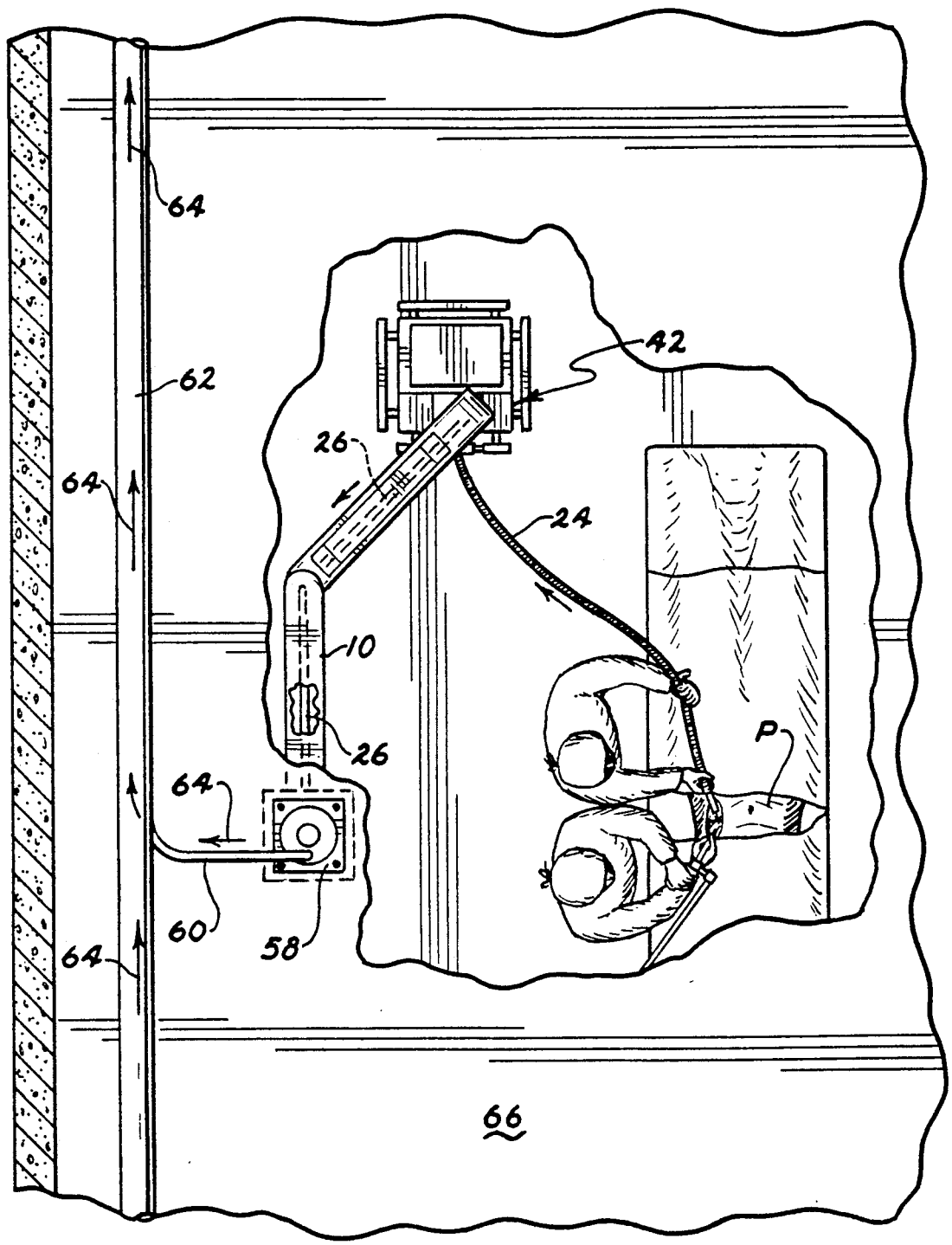
FIG. 3 shows a plan view through a broken-away portion of the ceiling of a typical hospital operating room equipped with the present invention, as it might appear in use.

Access to the system is afforded by a network of piping, beginning at the patient P with disposable flexible tubing 24, as shown in FIGS. 1 and 3. Flexible tubing 24, which should be disposed of after use, is available in a variety of diameters for varying procedures. For example, tubing having an inside diameter of ⅛ inch (3.125 mm) may be used for laparoscopies, while tubing having an inside diameter of 1⅛ inch (28.125 mm) may be used for removing scars or birthmarks. Extending within articulating arm 10 is smooth sided flexible tubing 26. It is important that tubing 26 have smooth sides to prevent the buildup of debris within the tubing. Tubing 26 has an inside diameter of 1¼ inch (31.25 mm) to accommodate adequately the largest size disposable tubing 24 that might be used with the system.

Figure 4:
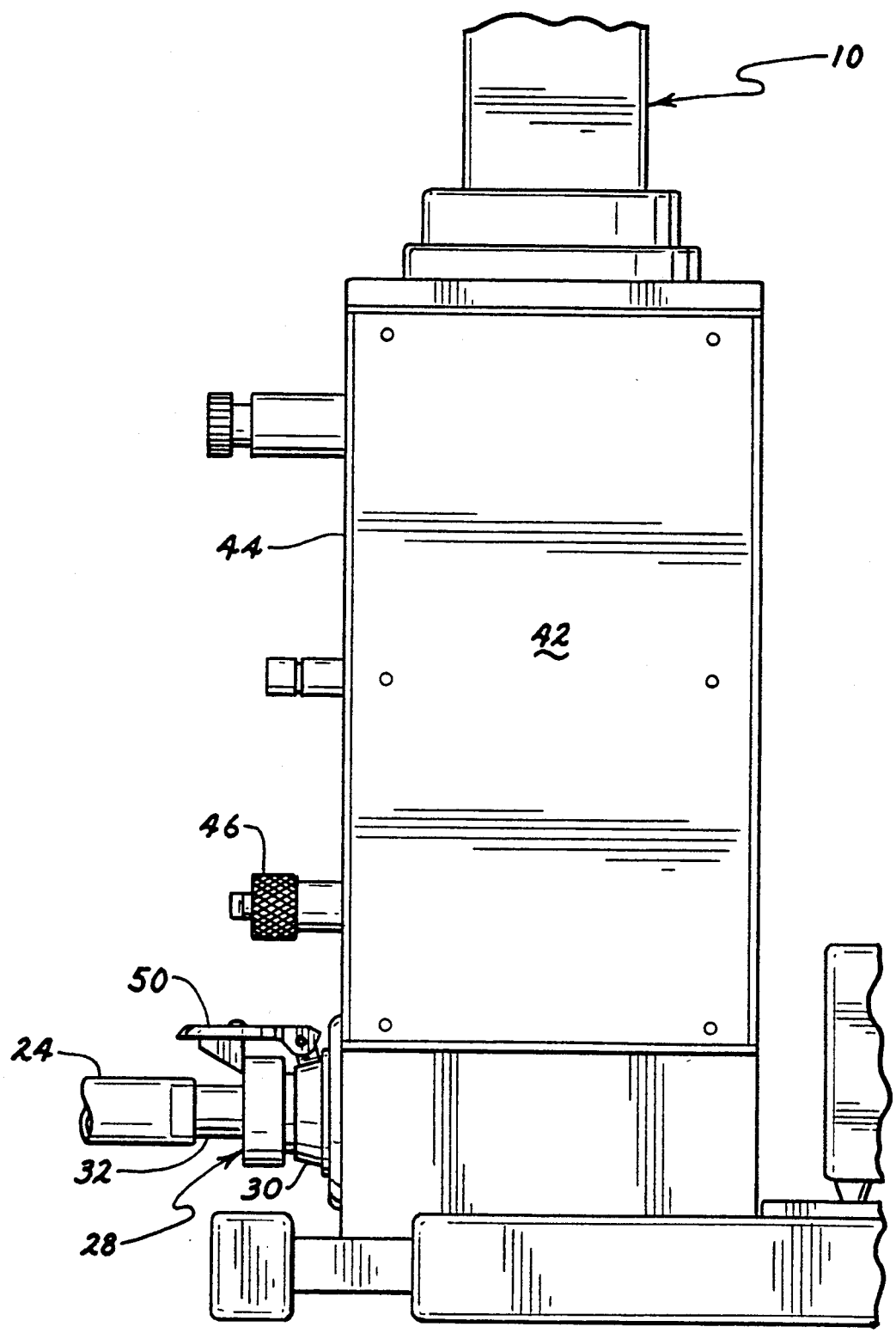
FIG. 4 shows a side view of the panel area of the articulating arm, to which is connected the disposable, flexible hose used with the present invention.
Figure 5:
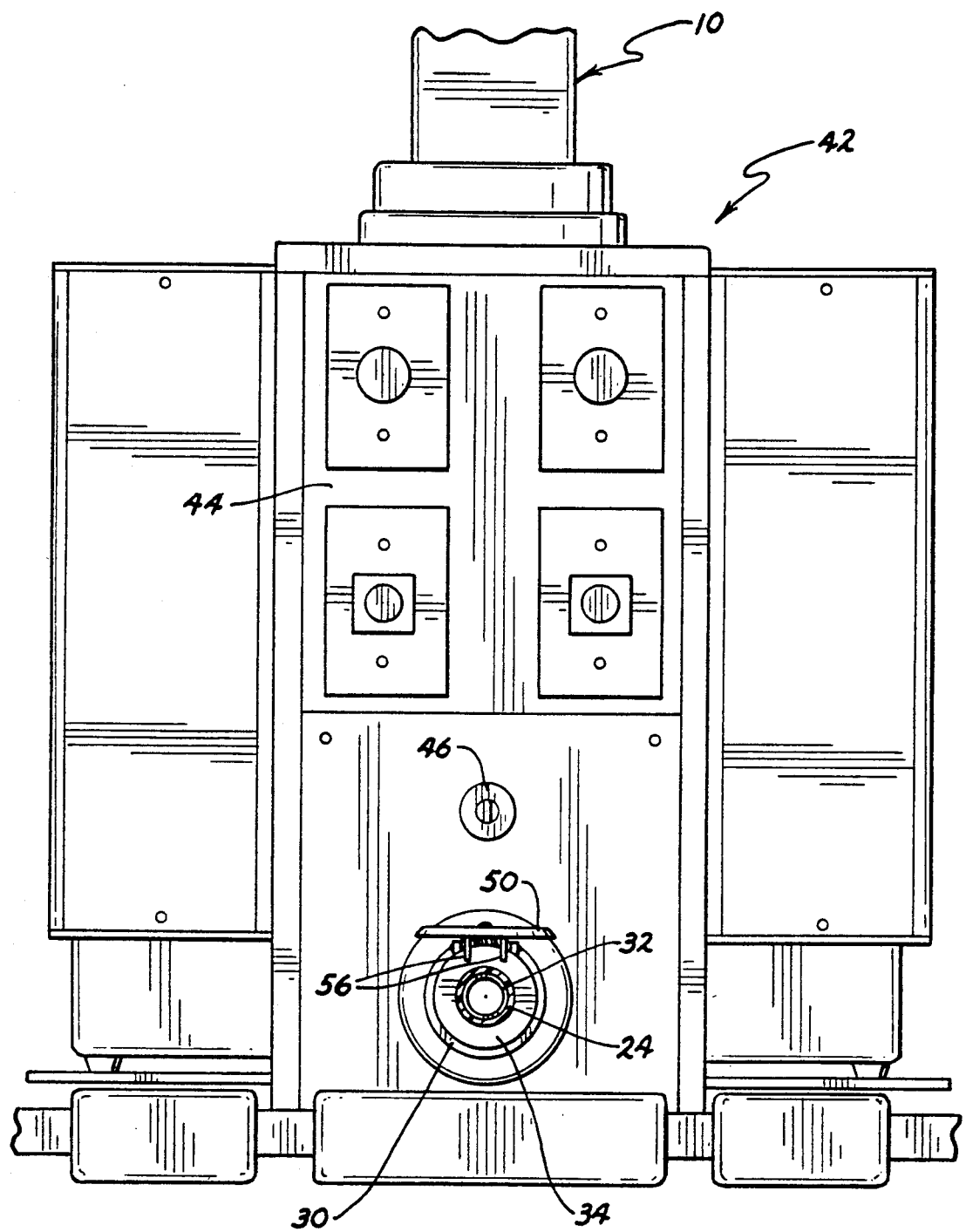
FIG. 5 shows a plan view of the control box of the articulating arm illustrated in FIG. 4.
Figure 6:
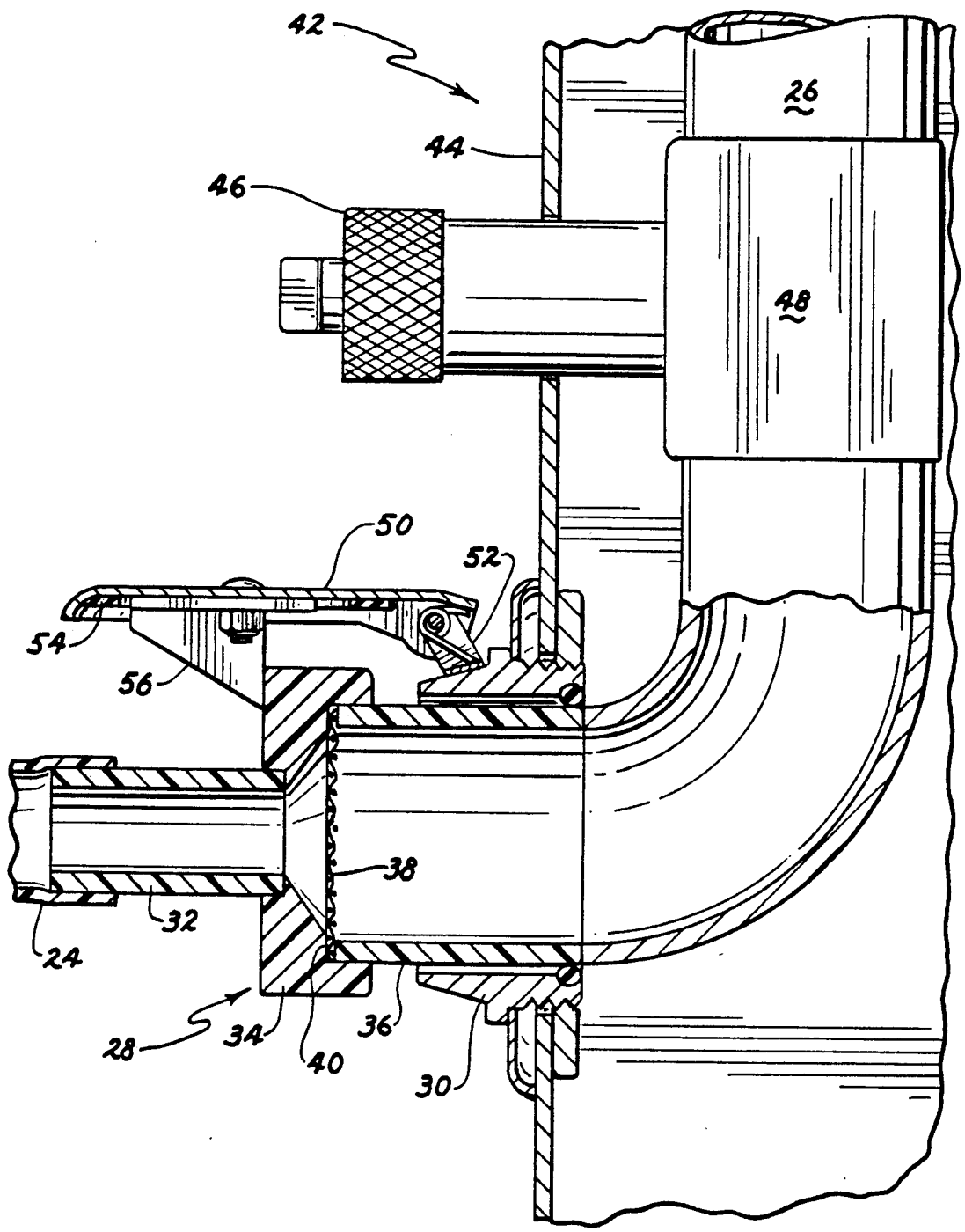
FIG. 6 is a partial section view similar to that of FIG. 4, showing the detail of the connector between the internal and external hoses of the present invention.

With particular reference to FIGS. 4-6, connection between disposable tubing 24 and smooth tubing 26 is accomplished by use of coupling assembly 28 connected as by friction fit to a connector 30. Coupling assembly 28 includes a flexible tubing engaging member 32 for engaging flexible tubing 24. Flexible tubing engaging member 32 fixedly engages tapered member 34, permitting flexible tubing 24 of reduced diameter to couple with smooth sided tubing 26. Coupling assembly 28 must include an engaging member 32 of suitable diameter to properly engage the size of flexible tubing 24 being used for the particular medical procedure being performed at the time. Thus a number of various coupling assemblies 28 need to be available providing an engaging member 32 corresponding with a different diameter of flexible tubing 24. Coupling assembly 28 also includes an arm engager 36 that slides into connector 30. As may be seen in FIG. 6, arm engager 36 bears against a screen member 38 contained within coupling assembly 28 between arm engager 36 and retaining wall segment 40 of tapered member 34. Screen member 38 is preferably approximately 1/16 inch (1.56 mm) thick, and serves to capture large items that may be drawn into flexible tubing 24 by the suction provided by the system. Such large items as sponges and needles, while they may be properly handled and disposed of by the system, must be accounted for during a surgery procedure, and it is therefore important that they be captured by screen member 38 so that a count may be made of them at the end of the procedure.

FIGS. 4 and 5 illustrate views of a typical control box 42 of an articulating arm 10, which, as may be seen in FIGS. 1 and 3, is located at the end of the articulating arm, and includes a control panel 44. FIG. 5 shows on the upper part of control panel 44 a typical arrangement of controls and nozzles, which may connect to pressurized gas lines containing $CO_2$ or $O_2$, or may include video input connections or access to other supplies or services routinely necessary for surgery procedures. The lower part of control panel 44 may typically appear similar to the upper portion, as illustrated in FIG. 5, but the present invention requires the use of at least an entire half of the control panel. For embodiments of the system that do not include articulating arm 10, control panel 44 may be attached to a wall or ceiling of the procedure room or to a medical gas column.

Also illustrated in FIGS. 4-6 is a control knob 46 for controlling the vacuum of the centralized laser plume evacuation system. The vacuum is infinitely variable between zero and eighty to ninety CFM (cubic feet per minute). Lower settings of approximately ten CFM are preferable for procedures such as laparoscopies that require smaller diameter hoses, since these procedures generally create a smaller plume and because the flexible tubing 24 used with this procedure is quite small in diameter, and larger vacuums tend to cause the hose to collapse. Higher settings of approximately eighty CFM are required for procedures such as removing scars or birthmarks, when flexible tubing 24 of larger diameter is used. As shown in FIG. 6, control knob 46 controls a standard ball valve 48 that controls the vacuum passing through smooth side flexible tubing 26 that passes through articulating arm 10.

Connector 30, when not in use, is covered by connector cover 50, which is biased toward the covering position by a spring 52. A round gasket 54, preferably of rubber, is included on the inner surface of connector cover 50, to seal the connector when not in use. It is important to include a gasket 54 to prevent air from leaking into the system since the vacuum producer 16 may be overworked and its reliability and efficiency reduced if air was permitted to leak into the system from connectors 30 of articulating arms 10 in operating rooms where the laser plume evacuation system was not in use. Connector cover 50 also includes at least one coupling retaining tooth 56, shown in FIGS. 5 and 6. Coupling retaining teeth 56 engage tapered member 34 of coupling assembly 28, as shown in FIG. 6, thereby retaining coupling assembly 28 in firm engaged relationship with connector 30.

With reference to FIGS. 1 and 3, the continuation of the piping system from the hospital operating room is illustrated, showing smooth sided flexible tubing 26 passing through articulating arm 10 and then through a ceiling mounting assembly 58 and connecting to branch 60, which in turn connects as by welding to main 62. It is important that all welded connections satisfy standards set for medical vacuum systems. The direction of air flow passing through the system is indicated by direction arrows 64. Branch 60 is preferably approximately 1¼ inch (31.25 mm) in diameter, and main 62 is preferably approximately six inches (150 mm) in diameter. Ceiling mounting assembly 58 is anchored to structural ceiling S, and main 62 is positioned between structural ceiling S and finished ceiling 66.

As illustrated in FIG. 2, centrifugal separator 12, vacuum producer 16 and HEPA filter 18 are preferably located in a single room such as a room containing other mechanical controls and assemblies, each device being easily accessible for maintenance and repair. Main 62 enters the room and feeds first into centrifugal separator 12. Centrifugal separator 12 forces air introduced therein to spin rapidly about the periphery of the tank, separating solid and liquid wastes from the gases introduced from main 62. The surviving gases leave centrifugal separator 12 through an opening in the top thereof, and enter secondary main 68. All solid and liquid wastes separated from the air introduced into centrifugal separator 12 are expelled from the tank into the sewage system by means of garbage pump 14. Before being discharged, however, the wastes are treated by a disinfectant solution. Centrifugal separator 12 may also be rinsed periodically by non-foaming disinfectant solutions. These disinfectant solutions are introduced into centrifugal separator 12 through disinfectant inlets 20. As shown in FIG. 2, there may be two such disinfectant inlets 20. The upper one permits of rinsing the centrifugal separator portion of the tank, while the lower one permits of disinfection of the contents at the bottom of the separator 12 that have been separated from the air passing through the tank.

Air is drawn through the system by vacuum producer 16, which may be simply a large fan. In a hospital setting where several operating rooms are provided with the plume evacuation system, for example, a twenty-five horsepower vacuum producer may provide adequate vacuum to power the system. Although FIG. 2 shows only one such vacuum producer 16, in an actual hospital setting it is advisable to include at least two such fans to ensure redundancy in case one of the fans fails. Further, an unlimited number of vacuum producers 16 may be provided in series to provide adequate vacuum to service a system of virtually any size. It is important to locate vacuum producer 16 after centrifugal separator 12 because the contaminants that are removed from the air stream by centrifugal separator 12 could have an adverse effect on vacuum producer 16 if not removed from the air first. To prevent damage to vacuum producer 16 or inefficient operation of the system, bleed valve 22 is provided on secondary main 68. Upon detecting that vacuum producer 16 is operating inefficiently or is in danger of being damaged due to insufficient air flow, bleed valve 22 will permit additional air to be introduced into secondary main 68. This condition might arise, for example, where many inlets are provided throughout a system, but none or only a few are being used, and little or no air is therefore entering the system from the inlets at each articulating arm 10.

Before being exhausted out of the hospital, the air in secondary main 68 passes through HEPA filter 18, which provides filtration that is approximately 99.9995% efficient. The preferred filters for this system are Guide Pack filters manufactured by American Air Filter Co. In an alternate embodiment, HEPA filter 18 may be replaced by an incinerator, which would be located outside of the hospital. The incinerator simply provides an alternative means for destroying any particulates or other contaminants remaining in the air after passing through centrifugal separator 12.

Figure 7:
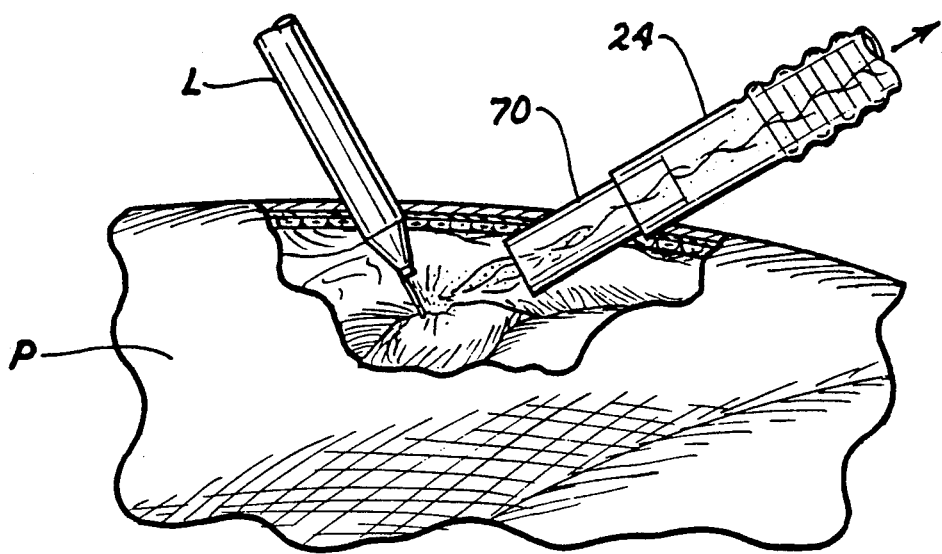
FIG. 7 shows a perspective view of the external hose of the present invention as it appears in a typical operating procedure.
Figure 8:
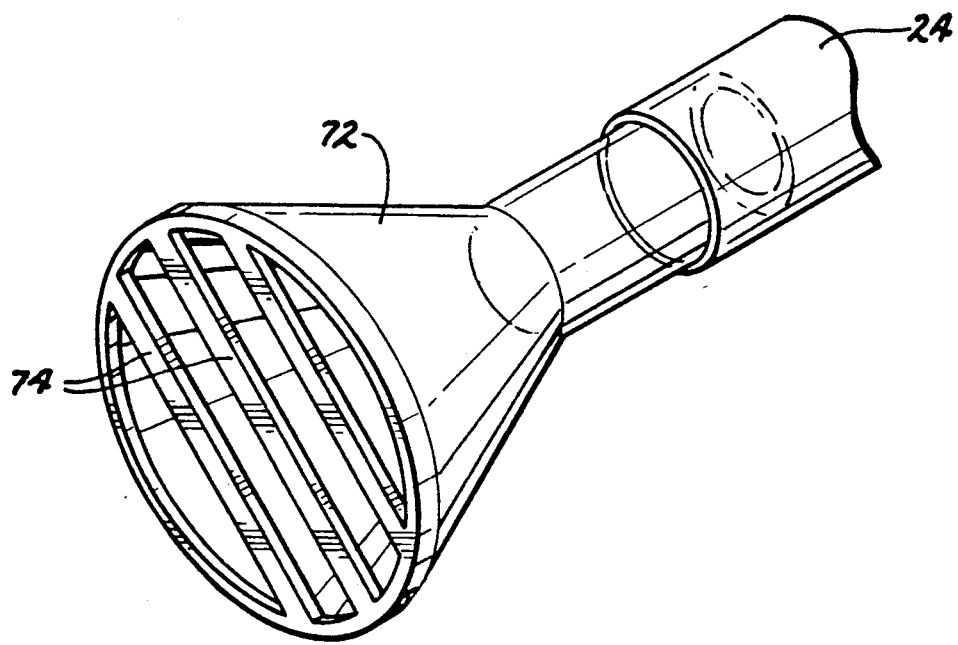
FIG. 8 shows a funnel adaptor usable with the plume-receiving end of the external hose of the present invention.

FIG. 7 illustrates an application of the laser plume evacuation system. While patient P is being operated on using laser wand L held by the surgeon, disposable flexible tubing 24, which may have an adaptor 70 attached to the inlet end thereof, is held in position by a nurse or other attendant during the operating procedure. Adaptor 70, which has walls that are more rigid than those of flexible tubing 24, slides into the end of flexible tubing 24, to help maintain a uniform opening at the end of the tube, where there is otherwise a tendency for tubing 24 to collapse due to the suction of the plume evacuation system. The adaptor may take the form of funnel shaped expander 72 illustrated in FIG. 8. Expander 72 includes at least one slot formed by strips 74 to regulate the amount of air entering expander 72, maintaining the level of the suction by diminishing the surface area.

In use, flexible tubing 24 is attached to coupling assembly 28, which is plugged into connector 30 on control panel 44 of articulating arm 10. Articulating arm 10 is positioned to be conveniently located relative to the area of patient P on which the procedure is to be performed. Connector cover 50 is positioned so that coupling retaining teeth 56 engage tapered member 34 of coupling assembly 28. Control knob 46 is adjusted to provide the appropriate level of vacuum for the procedure about to be performed. Next, the inlet end of flexible tubing 24, including adaptor 70, is held in position by an attendant within approximately two inches (50 mm) of the site of the medical procedure. While the procedure is being performed, flexible tubing 24 continues to be held in position. As the plume of airborne contaminants rises from the site of the medical procedure, the plume is drawn into flexible tubing 24, through which it passes to smooth sided flexible tubing 26, branch 60 and main 62. All airborne contaminants are thus drawn out of and away from the operating room.

After leaving the operating room, the airborne contaminants are drawn into the centrifugal separator 12. There, the solid and liquid contaminants are separated out of the air, and gather at the bottom of the tank that comprises the housing of centrifugal separator 12. These solid and liquid contaminants may be treated by non-foaming liquid disinfectant introduced into the tank through disinfectant inlets 20 before being discharged from the tank by garbage pump 14. The air leaving centrifugal separator 12 is exhausted into secondary main 68, drawn through vacuum producer 16 and forced through high efficiency filter 18 before being exhausted to the atmosphere outside of the building housing the medical procedure rooms.

While the preferred embodiments of the invention have been described, it should be understood that various changes, adaptations and modifications may be made therein without departing from the spirit of the invention and the scope of the appended claims.

What is claimed is:

1. A method of using a centralized system for removing airborne contaminants from the site of a medical procedure being performed in one of a plurality of medical procedure rooms connected to the centralized system, the airborne contaminants being the result of the medical procedures performed in the medical procedure rooms, the centralized system including at least one access outlet in each medical procedure room, a first flexible hose having a first end and a second end, the first flexible hose being attachable to the access outlet, piping for transporting the airborne contaminants from the medical procedure rooms, vacuum means for creating a suction that draws the airborne contaminants from the medical procedure rooms via the piping, and means for filtering the airborne contaminants from the air drawn from the medical procedure room, comprising the steps of:

releasably attaching the first end of the first flexible hose to the access outlet;

extending the second end of the first flexible hose to the location of the medical procedure; and holding the second end of the first flexible hose adjacent the location of the medical procedure, whereby the airborne contaminants generated by the medical procedure are drawn out of and away from the medical procedure room through the first flexible hose and the piping by the suction generated by the vacuum means.

2. The method of using a centralized system for removing airborne contaminants described in claim 1, comprising the further step of:

adjusting a control knob to regulate the suction of the centralized system for removing airborne contaminants.

3. The method of using a centralized system for removing airborne contaminants described in claim 2, further comprising:

means for delivery of medical procedure supplies to the area of the medical procedure room where the medical procedure is being performed, whereby the access outlet is mounted to said medical supply delivery means; and a second flexible hose attached to said medical supply delivery means, extending between the access outlet and the piping.

4. The method of using a centralized system for removing airborne contaminants described in claim 3, wherein said medical supply delivery means comprises:

an articulating arm suspended from the ceiling of the medical procedure room.

5. The method of using a centralized system for removing airborne contaminants described in claim 4, comprising the further step of:

locating said articulating arm in a convenient position adjacent the location of the medical procedure.

6. The method of using a centralized system for removing airborne contaminants described in claim 5, wherein said articulating arm further comprises:

a control box having a control panel mounted thereto, the access outlet and said control knob for regulating the suction of the centralized system for removing airborne contaminants being mounted on said control panel.

7. The method of using a centralized system for removing airborne contaminants described in claim 6, comprising the further step of:

positioning an access outlet cover member to securely retain the first end of the first flexible hose to the access outlet.

8. The method of using a centralized system for removing airborne contaminants described in claim 7, comprising the further step of:

positioning a rigid cylindrical adaptor on the second end of the first flexible hose, whereby said rigid cylindrical adaptor prevents the collapse of the wall of the first flexible hose, maintaining an opening of constant area for proper suction of the airborne contaminants produced by the medical procedure.

9. The method of using a centralized system for removing airborne contaminants described in claim 4, comprising the further steps of:
attaching a coupling assembly to the first end of the first flexible hose before releasably attaching the first end of the first flexible hose and the coupling assembly to the access outlet; and
positioning an access outlet cover member to securely retain the coupling assembly to the access outlet.

10. The method of using a centralized system for removing airborne contaminants described in claim 1, further comprising:
a support structure for adjustably positioning the first end of the first flexible hose near the area of the medical procedure being performed in the medical procedure room.

11. The method of using a centralized system for removing airborne contaminants described in claim 8, wherein said support structure comprises:
an articulating arm.

12. The method of using a centralized system for removing airborne contaminants described in claim 11, comprising the further step of:
locating said articulating arm in a convenient position adjacent the location of the medical procedure.

13. A centralized system for removing airborne contaminants from the site of at least one medical procedure being performed in at least one of a plurality of medical procedure rooms connected to the centralized system, the airborne contaminants being the result of the medical procedures performed in the medical procedure rooms, comprising:
at least one inlet means for extracting the airborne contaminants from the site of the medical procedures;
piping means connected to said inlet means for transporting the airborne contaminants from the site of the medical procedures;
filter means connected to said piping means; and
vacuum means connected to said piping means, whereby air is drawn into said inlet means and transported out of the medical procedure rooms via said piping means.

14. The centralized system described in claim 13, further comprising:
support means for locating said inlet means relatively near the site of the medical procedure.

15. The centralized system described in claim 14, wherein said support means comprises:
an articulating arm suspended from the ceiling of the medical procedure room.

16. A centralized system for removing airborne contaminants from the site of at least one medical procedure being performed in at least one of a plurality of medical procedure rooms connected to the centralized system, the airborne contaminants being the result of the medical procedures performed in the medical procedure rooms, comprising:
at least one access outlet fixedly positioned in each medical procedure room, said access outlet providing access to the centralized system for removing airborne contaminants;
a first flexible hose member attachable to and extending from said access outlet to the area of the medical procedure being performed in the medical procedure room;
piping means for transporting the airborne contaminants from the medical procedure room, said piping means being connected to said access outlet; and
vacuum means connected to said piping means, whereby said vacuum means creates a suction that draws air from the medical procedure room, through said first hose member and out of the medical procedure room via said piping means.

17. The centralized system for removing airborne contaminants described in claim 16, further comprising:
filter means connected to the plurality of medical procedure rooms by said piping means.

18. The centralized system for removing airborne contaminants described in claim 17, wherein said filter means comprises:
a centrifugal separator tank, whereby solid and liquid contaminants are separated from the other airborne particles removed from the medical procedure rooms.

19. The centralized system for removing airborne contaminants described in claim 18, wherein said filter means further comprises:
an air filter for removing minute airborne particles not eliminated from the exhausted air by said centrifugal separator tank.

20. The centralized system for removing airborne contaminants described in claim 16, further comprising:
means for delivery of medical procedure supplies to the area of the medical procedure room where the medical procedure is being performed, said access outlet being mounted to said medical supply delivery means; and
a second flexible hose member attached to said medical supply delivery means, extending between said access outlet and said piping means.

21. The centralized system for removing airborne contaminants described in claim 20, wherein said medical supply delivery means comprises:
an articulating arm suspended from the ceiling of the medical procedure room.

22. The centralized system for removing airborne contaminants described in claim 21, wherein said articulating arm further comprises:
a control box having a control panel mounted thereto, said access outlet being mounted on said control panel.

23. The centralized system for removing airborne contaminants described in claim 22, further comprising:
valve means for controlling the passage of airborne contaminants through said second flexible hose member; and
a control knob mounted to said control panel for adjusting said valve means, whereby said control knob permits the adjustment of the amount of suction provided by said vacuum means.

24. The centralized system for removing airborne contaminants described in claim 23, further comprising:
filter means connected to the plurality of medical procedure rooms by said piping means.

25. The centralized system for removing airborne contaminants described in claim 24, wherein said filter means comprises:
a centrifugal separator tank, whereby solid and liquid contaminants are separated from the other airborne particles removed from the medical procedure rooms.

26. The centralized system for removing airborne contaminants described in claim 25, wherein said filter means further comprises:
   an air filter for removing minute airborne particles not eliminated from the exhausted air by said centrifugal separator tank.

27. The centralized system for removing airborne contaminants described in claim 16, further comprising:
   a coupling assembly removably attachable to said first flexible hose member and matable with said access outlet, whereby said first flexible hose member is removably engaged with said piping means by said coupling assembly.

28. The centralized system for removing airborne contaminants described in claim 27, wherein said coupling assembly further comprises:
   a screen member extending across the opening defined by said coupling assembly, whereby said screen member obstructs the passage of oversized items into the centralized system, permitting the removal of such oversized items from said coupling assembly.

29. The centralized system for removing airborne contaminants described in claim 27, wherein said access outlet further comprises:
   a connector member;
   a connector cover hingedly connected to said connector member; and
   at least one coupling assembly retaining tooth, whereby said at least one coupling assembly retaining tooth engages said coupling assembly, securely retaining said coupling assembly in engaged relationship with said piping means.

30. The centralized system for removing airborne contaminants described in claim 16, further comprising:
   a rigid cylindrical adaptor inserted in the end of said first flexible hose adjacent the medical procedure, whereby said rigid cylindrical adaptor prevents the collapse of the wall of said first flexible hose, maintaining an opening of constant area for proper suction of the airborne contaminants produced by the medical procedure.

31. The centralized system for removing airborne contaminants described in claim 30, wherein said rigid cylindrical adaptor further comprises:
   a funnel shaped portion expanding to an opening having a diameter greater than that of said first flexible hose; and
   at least one rigid strip across said opening of said funnel shaped portion, whereby said at least one rigid strip reduces the open surface area of said opening of said funnel shaped portion, thereby maintaining an open surface area substantially equivalent to that of said first flexible hose.

32. The centralized system for removing airborne contaminants described in claim 16, further comprising:
   a support structure for adjustably positioning said first flexible hose member near the area of the medical procedure being performed in the medical procedure room.

33. The centralized system for removing airborne contaminants described in claim 32, wherein said support structure further comprises:
   an articulating arm.

34. The centralized system for removing airborne contaminants described in claim 33, wherein said articulating arm further comprises:
   a control box having a control panel mounted thereto, said access outlet being mounted on said control panel; and
   a second flexible hose member attached to said articulating arm, extending between said access outlet and said piping means.

35. The centralized system for removing airborne contaminants described in claim 34, further comprising:
   valve means for controlling the passage of airborne contaminants through said second flexible hose member; and
   a control knob mounted to said control panel for adjusting said valve means, whereby said control knob permits the adjustment of the amount of suction provided by said vacuum means.

36. The centralized system for removing airborne contaminants described in claim 34, wherein:
   said second flexible hose member runs internally to said articulated arm.

* * * * *

UNITED STATES PATENT AND TRADEMARK OFFICE
CERTIFICATE OF CORRECTION

PATENT NO. : 5,264,026
DATED : November 23, 1993
INVENTOR(S) : Gwen A. Paul

It is certified that error appears in the above-identified patent and that said Letters Patent is hereby corrected as shown below:

col 9, claim 9, ln 4, delete "4" after the word "claim" and insert -- 1 -- therefore.

col 9, claim 11, ln 22, delete "8" after the word "claim" and insert -- 10 -- therefore.

Signed and Sealed this

Thirty-first Day of May, 1994

Attest:

BRUCE LEHMAN

*Attesting Officer*     *Commissioner of Patents and Trademarks*